United States Patent [19]
Tsujita et al.

[11] Patent Number: 6,110,159
[45] Date of Patent: Aug. 29, 2000

[54] DEVICE FOR DISPOSING EXCREMENT

[75] Inventors: Hiromitsu Tsujita; Kiichi Komatsu; Hisashi Yamatoya, all of Tokyo, Japan

[73] Assignee: Niles Parts Co., Ltd., Tokyo, Japan

[21] Appl. No.: 09/116,540

[22] Filed: Jul. 16, 1998

[30]     Foreign Application Priority Data

Jul. 29, 1997  [JP]  Japan .................................. 9-218006

[51] Int. Cl.⁷ ................................................ A61F 13/15
[52] U.S. Cl. ........................ 604/387; 604/313; 604/316; 604/289; 604/334; 604/341; 604/348; 4/420.2; 4/420.4; 4/443; 4/448; 4/666
[58] Field of Search ................... 604/313, 316, 604/289, 334, 341, 387.1; 4/666, 443–448

[56]           References Cited

U.S. PATENT DOCUMENTS

| | | | |
|---|---|---|---|
| Re. 28,405 | 5/1975 | Sollerud | 448/68 |
| 1,684,047 | 9/1928 | Stoven | 119/852 |
| 1,970,013 | 8/1934 | Mahmourian | 128/257 |
| 2,228,698 | 1/1941 | Fitches | 119/1 |
| 2,612,892 | 10/1952 | Beatman | 601/6 |
| 2,691,173 | 10/1954 | Smith | 4/1 |
| 2,749,558 | 6/1956 | Lent et al. | 4/10 |
| 3,034,131 | 5/1962 | Lent | 2/2.1 |
| 3,713,423 | 1/1973 | Sparr, Sr. | 119/1 |
| 4,200,102 | 4/1980 | Duhamel et al. | 128/286 |
| 4,791,686 | 12/1988 | Taniguchi et al. | 4/448 |
| 4,900,316 | 2/1990 | Yamamoto | 604/313 |
| 4,982,462 | 1/1991 | Wada | 4/546 |
| 5,358,494 | 10/1994 | Svedman | 604/313 |
| 5,363,514 | 11/1994 | Lee | 4/455 |
| 5,466,229 | 11/1995 | Elson et al. | 604/317 |
| 5,525,161 | 6/1996 | Milocco | 134/18 |
| 5,624,416 | 4/1997 | Schatz | 604/313 |
| 5,662,677 | 9/1997 | Wimmer | 604/201 |
| 5,697,920 | 12/1997 | Gibbons | 604/289 |
| 5,735,833 | 4/1998 | Olson | 604/23 |
| 5,792,125 | 8/1998 | Webb | 604/319 |
| 5,809,586 | 9/1998 | Kitamura | 4/443 |
| 5,826,282 | 10/1998 | Matsumoto et al. | 4/420.4 |
| 5,842,237 | 12/1998 | Hargest et al. | 4/449 |
| 5,843,052 | 12/1998 | Benja-Athon | 604/289 |
| 5,941,859 | 8/1999 | Lerman | 604/313 |
| 6,009,570 | 1/2000 | Hargest et al. | 4/449 |

*Primary Examiner*—John G. Weiss
*Assistant Examiner*—Paul A. Shanoski
*Attorney, Agent, or Firm*—Ronald P. Kananen; Rader, Fishman & Grauer

[57]              ABSTRACT

A device for disposing excrement comprising: a diaper cup 1 for enveloping a lumbar/gluteal region of a human body; and a device body C connected to the diaper cup 1 for supplying washing water to the inside of the diaper cup and for sucking excrements and sewage from the inside of the diaper cup 1. The device body C includes: a suction motor 21 for establishing a vacuum to suck the excrements and the sewage; a water supply pump 5 for supplying the washing water; and a sequencer 12 for controlling the suction motor 21 and the water supply pump 5. The sequencer 12 includes intermittent drive means S4 to S8 or S24 to S29 for controlling the drive of the water supply pump 5 by setting time parameters according to the sense signals of the feces sensor 109 and the urine sensor 114. The device washes the excrements in the diaper cup efficiently in a mode matching the kind of the excrements in the diaper cup, without making the diaper cup wearer feel uncomfortable, by discriminating the excrement kind with the feces sensor and the urine sensor, and promotes the excretion of a patient who could not otherwise excrete, by stimulating the patient properly with intermittent injections of washing water.

15 Claims, 4 Drawing Sheets

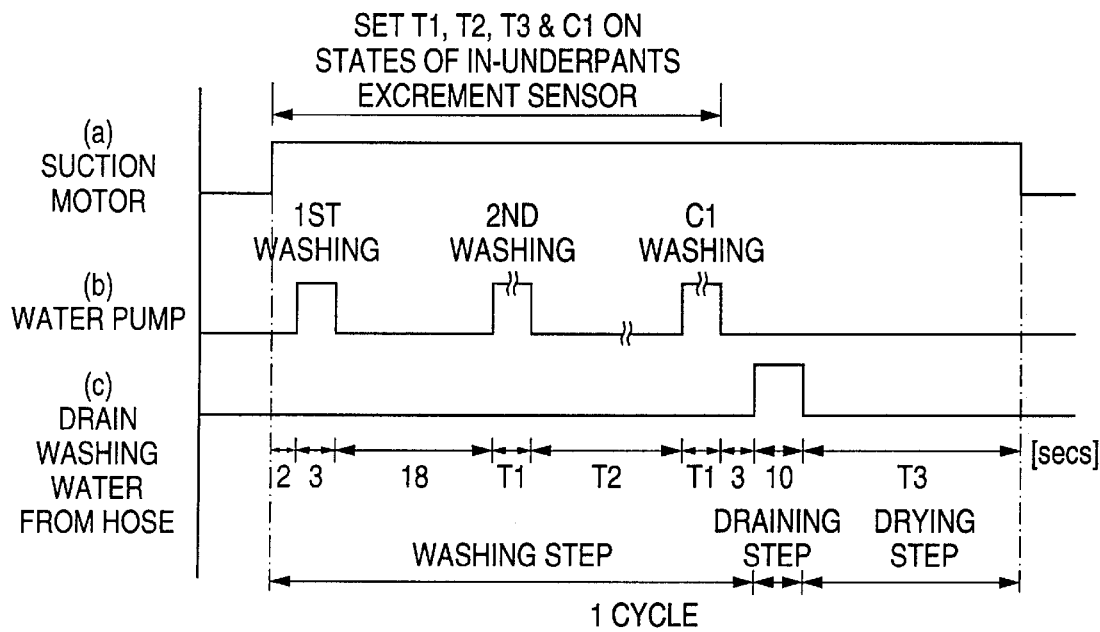
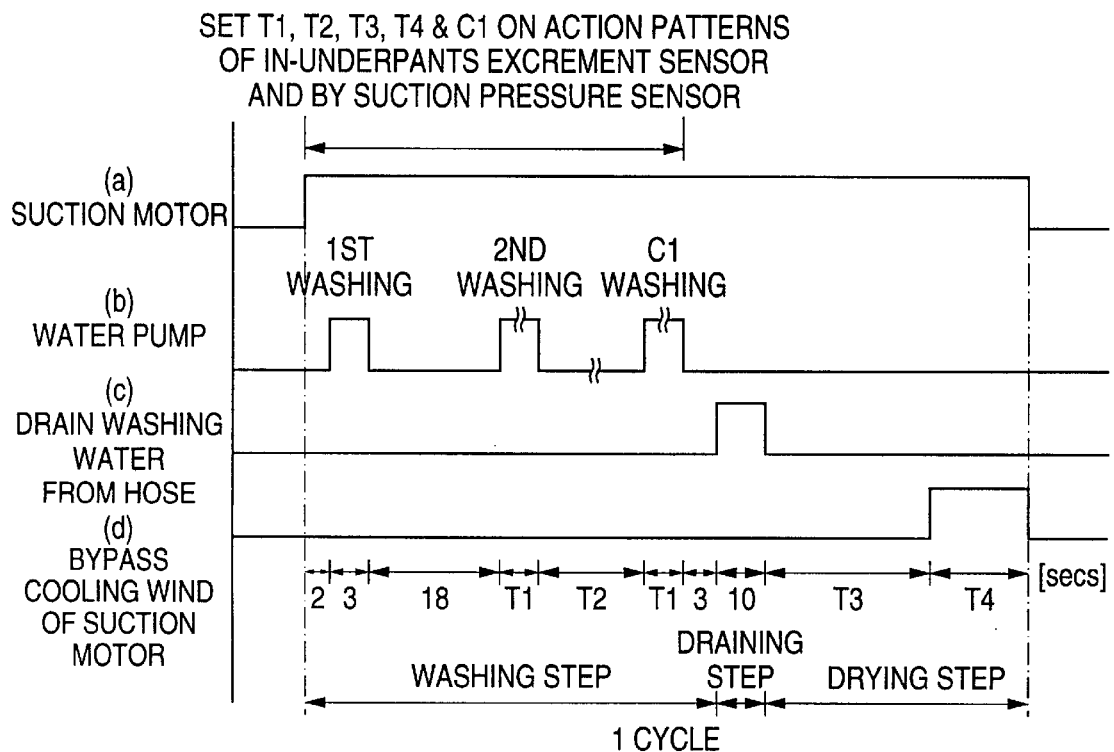

DEVICE FOR DISPOSING EXCREMENT

BACKGROUND OF THE INVENTION

1. Field of the Invention

The present invention relates generally to a device for disposing excrement to be applied to a bedridden patient in a hospital or the like. More particularly, the present invention relates to a device for disposing excrement capable of automatically disposing the excrements, when excreted by the patient or the like in bed, and washing the private parts of the patient soiled with the excrements.

2. Description of the Related Art

A conventional device for disposing excrement is disclosed, for example, in Unexamined Published Japanese Patent Application No. 4-364841. This conventional device has a structure in which the lumbar/gluteal region of a human body is enveloped with a diaper cup made of a soft insulating material and in which the excrements, as excreted into the diaper cup, are washed with washing water and discharged to the outside of the diaper cup by a pump. Various hoses are connected to the diaper cup, including a washing water supply hose and an excrement suction hose. Chords of sensors are also connected to the diaper cup for detecting the excrements in the diaper cup.

In the conventional device, however, the washing water is supplied improperly to the inside of the diaper cup such that the wearer of the diaper cup is caused to feel uncomfortable or to lose a desire for defecation.

SUMMARY OF THE INVENTION

The present invention has been made to solve the problems with the conventional device for disposing excrement described above.

An object of the present invention is to make it possible to wash the excrements in a diaper cup efficiently in a mode matching the kind of excrements in the diaper cup, without making the diaper cup wearer feel uncomfortable, by discriminating the excrement kind with a feces sensor and a urine sensor, and to promote the excretion of a patient who could not otherwise excrete, by stimulating the patient properly with intermittent injections of washing water.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

In accordance with the present invention, in order to solve the problems described above, a device for disposing excrement is provided, comprising: a diaper cup for enveloping a lumbar/gluteal region of a human body; and a system body connected to the diaper cup for supplying washing water to the inside of the diaper cup and for sucking the excrements and sewage from the inside of the diaper cup. The device for disposing excrement is characterized in that the system body includes: a suction motor for establishing a vacuum to suck the excrements and the sewage; a water supply pump for supplying the washing water; and a sequencer for controlling the suction motor and the water supply pump; and in that the sequencer includes intermittent drive means for controlling the drive of the water supply pump intermittently.

According to another aspect of the present invention, the sequencer includes continuous drive means for controlling the drive of the suction motor continuously when the drive of the water supply pump is intermittently controlled by the intermittent drive means.

According to another aspect of the present invention, the sequencer includes continuous drive means for controlling the drive of the suction motor to start and transfer to a continuous one by raising the rotating speed of the suction motor gradually.

According to another aspect of the present invention, the diaper cup includes a feces sensor and a urine sensor, and the sequencer includes intermittent drive means for controlling the drive of the water supply pump intermittently in a mode according to the sense signals of the feces sensor and the urine sensor.

According to another aspect of the present invention, the sequencer includes intermittent drive means for controlling the drive of the water supply pump intermittently by changing the intermittent drive mode of the water supply pump between the case in which the feces sensor senses feces, and the case in which the urine sensor senses urine.

According to another aspect of the present invention, the sequencer includes intermittent drive means for changing the time period per water supply of the water supply pump by setting time parameters according to the sense signals of the feces sensor and the urine sensor.

According to another aspect of the present invention, the sequencer includes initial drive means for starting the intermittent drive of the water supply pump immediately after the drive start of the suction motor.

BRIEF DESCRIPTION OF THE DRAWINGS

The present invention will become more clearly appreciated as the disclosure of the invention is made with reference to the accompanying drawings. In the drawings:

FIG. 4 is a first time chart illustrating the actions that are based on the flow chart shown in FIG. 2.

FIG. 5 is a second time chart illustrating the actions that are based on the flow chart shown in FIG. 3.

DETAILED DESCRIPTION OF THE INVENTION

Figure 1:
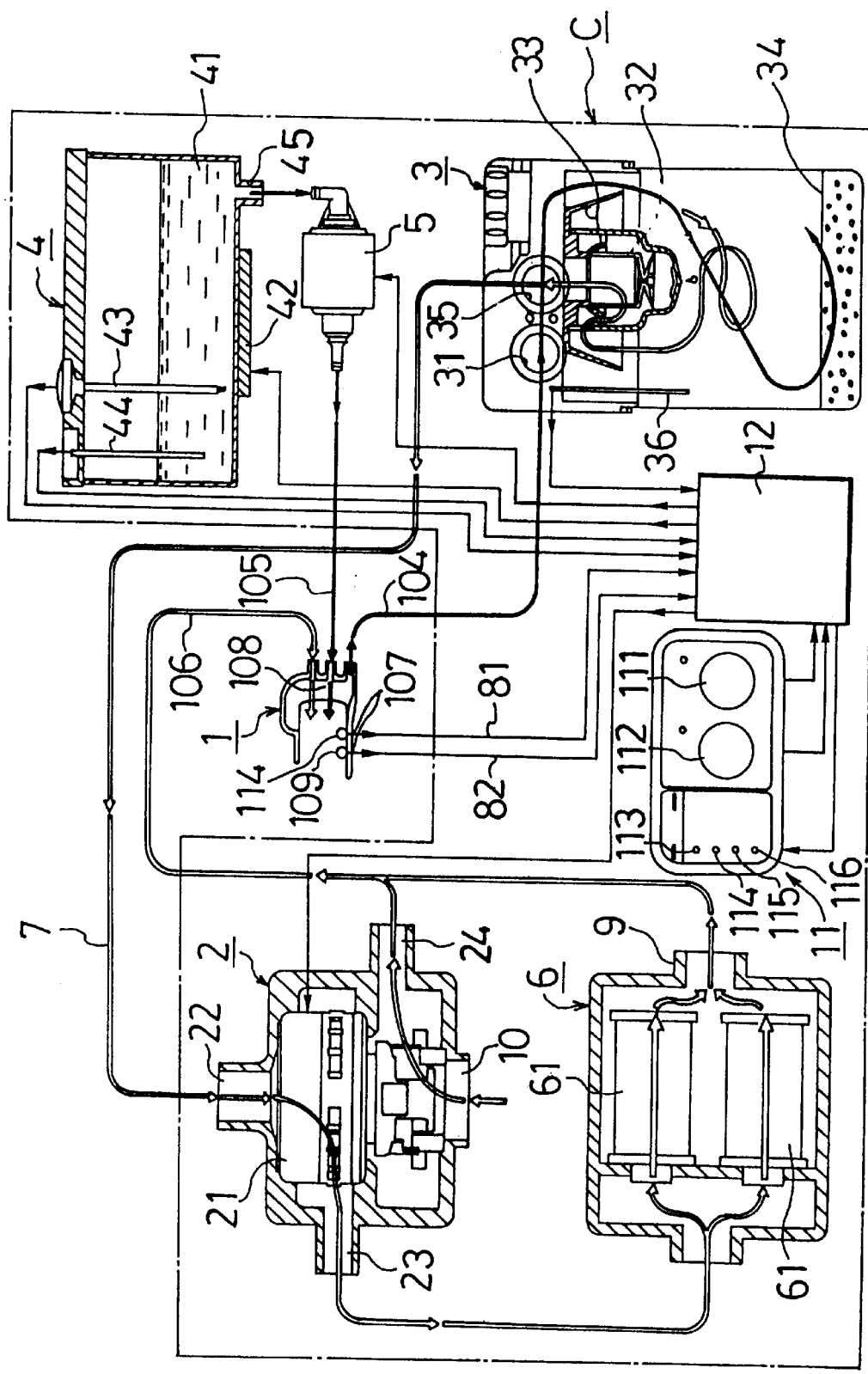
FIG. 1 is a block diagram showing a preferred embodiment of the present invention.

A preferred embodiment of the present invention will now be described in detail with reference to FIGS. 1 to 5 of the accompanying drawings.

Reference numeral 1 appearing in the drawings designates a diaper cup. The diaper cup 1 envelops the lumbar/gluteal region of a person to be nursed, such as a hospital patient or a bedridden old person, and is equipped therein with a feces sensor 109 and a urine sensor 114. The feces sensor 109 uses a photo-reflector for detecting an excrement excreted by the nursed person and a Cds cell for detecting the attachment/detachment of the diaper cup 1. The feces sensor 109 is disposed near a washing water injecting nozzle 108. The Cds cell detects a change in illuminance indicating that the diaper cup 1 is detached from the lumbar/gluteal region of the nursed person, and inactivates the device to prevent the washing water from being injected erroneously when the diaper cup 1 is detached.

On the other hand, the urine sensor 114 detects the urine excreted by the nursed person, and is constructed of a pair of electrodes supplied with an AC voltage of, for example, 2.5 Vp-p. The electric current to flow between the electrodes of the urine sensor 114 is so minute (about several micro amperes) that it is not detrimental to the nursed person in the least.

In the diaper cup 1, the feces sensor 109 and the urine sensor 114 are connected from a sensor coupler 107 via sensor signal lines 81 and 82 with a sequencer 12 of a system body C. Moreover, the diaper cup 1 is connected via an excrement suction hose 104 to an excrement tank 3 of the system body C, via a washing water supply hose 105 and through a water supply pump 5 to a warm water tank 4 of the system body C, and further via a warm wind hose 106 to a suction motor 21 and a filter box 6 in a vacuum motor housing 2 of the device body C.

The device body C is connected to the diaper cup 1 to supply the washing water to the inside of the diaper cup 1 and to suck the excrements and the sewage from the inside of the diaper cup 1. The device body C is equipped with the vacuum motor housing 2, the excrement tank 3, the warm water tank 4, the water supply pump 5, the filter box 6, a control panel 11 and the sequencer 12. The device body C is contoured by a box having casters, and the control panel 11 is mounted on the outer side of the device body C.

The vacuum motor housing 2 has the suction motor 21 packaged therein for establishing a vacuum to suck the excrements and the sewage, and is provided with: a suction port 22 connected via a vacuum hose 7 to the excrement tank 3; a first discharge port 23 for discharging the air (referred to as the "working wind"), as sucked from the suction port 22, to the filter box 6; a motor cooling suction pipe 10 for sucking the ambient air; and a second discharge port 24 for discharging the ambient air sucked from the motor cooling suction pipe 10. The air, as discharged from the second discharge port 24, is warmed by the heat generated by the suction motor 21 and is mixed with the deodorized working wind discharged from an air discharge pipe 9 of the filter box 6 so that the mixed wind is blown to the diaper cup 1 by the warm wind hose 106.

The device of the present invention has a running noise as low as possible so that it can be used in a relatively quiet room without making the patient uncomfortable. The running noise is kept low by mounting vibration proofing rubber elements on the suction motor 21 or by equipping the vacuum motor housing 2 with a silencer mechanism employing the muffler technique of an automobile. The filter box 6 has an air cleaning active carbon filter 61 packaged therein so that it is also effective for suppressing the noise.

The excrement tank 3 is for reserving the excrements, as sent from the diaper cup 1 via the excrement suction hose 104. The excrement tank 3 is provided with: a suction port 31 connected to the excrement suction hose 104; a cyclone mechanism 32 for separating the heavier excrements and washing water and the lighter working wind efficiently by the centrifugal force by swirling the working wind, as fed from the suction port 31, helically in the excrement tank 3; a separator 33 for separating the mist of the excrements and washing water, as contained in the working wind, by bringing it into collision; a discharge port 35 for discharging the working wind, as cleared of excrements 34, to the vacuum hose 7; and an excrement quantity sensor 36 for detecting the excrements 34 when limited to a predetermined quantity.

The warm water tank 4 is for supplying the diaper cup 1 with warm water. The tank 4 is equipped with: a heater 42 for heating and keeping the warm water 41; a thermometer 43 for confirming the water temperature; and a water level sensor 44 that functions as a temperature sensor. The warm water 41, as reserved in the warm water tank 4, is fed from a discharge port 45 through the water supply pump 5 to the diaper cup 1. However, the warm water 41, as fed to the diaper cup 1, has lost its temperature by several degrees while being fed. It is, therefore, advisable that the warming temperature of the warm water 41 reserved in the warm water tank 4 is set in advance at such a higher level that the warm water to be injected into the diaper cup 1 may take a proper temperature. The water supply pump 5 is a general solenoid valve and requires no specific description.

The control panel 11 is equipped with a start switch 111 and an interrupt switch 112 to be operated by a nursing person or the like for taking care of the nursed person. The control panel 11 also includes alarm lamps 113, 114, 115 and 116 for indicating the various states of the device, including the warm water supply, full excrement, warm water overheat and abnormal suction states.

The sequencer 12 is equipped with: a one-chip microcomputer (not shown) which has stored programs for controlling the suction motor 21, the water supply pump 5 and the heater 42 in accordance with input signals coming from the various sensors, including the feces sensor 109, the urine sensor 114, the excrement quantity sensor 36, the temperature sensor 43 and the water level sensor 44, and the start switch 111 and the interrupt switch 112 of the control panel 11; an I/O interface (not-shown) for processing the input/output signals of the one-chip microcomputer; and a driver circuit (not-shown) for driving the suction motor 21, the water supply pump 5, the heater 42, and the individual alarm lamps 113, 114, 115 and 116 of the control panel 11.

With reference to the flow charts shown in FIGS. 2 and 3, the programs stored in the one-chip microcomputer of the sequencer 12 will now be described. The program shown in FIG. 3 is slightly improved from that shown in FIG. 2 but has substantially the same basic contents. The sequencer 12 is provided in its program with intermittent drive means for controlling the drive of the water supply pump 5 intermittently. More specifically, the intermittent drive means is provided for changing the water supply time period per action of the water supply pump by setting time parameters according to the sense signals of the feces sensor 109 and the urine sensor 114. The program of the intermittent drive means is exemplified by steps S4 to S8 of the flow chart of FIG. 2 or by steps S24 to S29 of the flow chart of FIG. 3.

The sequencer 12 is further provided with continuous drive means for controlling the drive of the suction motor 21 continuously when the drive of the water supply pump 5 is intermittently controlled by the intermittent drive means. The program of the continuous drive means is exemplified by steps S3 and S11 of the flow chart of FIG. 2 or by steps S23 and S33 of the flow chart of FIG. 3.

The sequencer 12 is further provided with continuous drive means for starting the drive into a continuous one by raising the rotating speed of the suction motor 21. The program of the continuous drive means is exemplified by step S23 of the flow chart of FIG. 3.

The sequencer 12 is further provided with initial drive means for starting the intermittent drive of the water supply pump 5 immediately after the drive start of the suction motor 21. This initial drive means is exemplified by step S24 of the flow chart of FIG. 3.

The sequencer 12 is further provided with final drive means for blowing the cooling wind to the diaper cup 1. The cooling wind has been previously warmed by the heat generated by the suction motor 12 for a predetermined time period before the suction motor 21 is stopped. This final drive means is exemplified by step S32 of the flow chart of FIG. 3.

Figure 2:
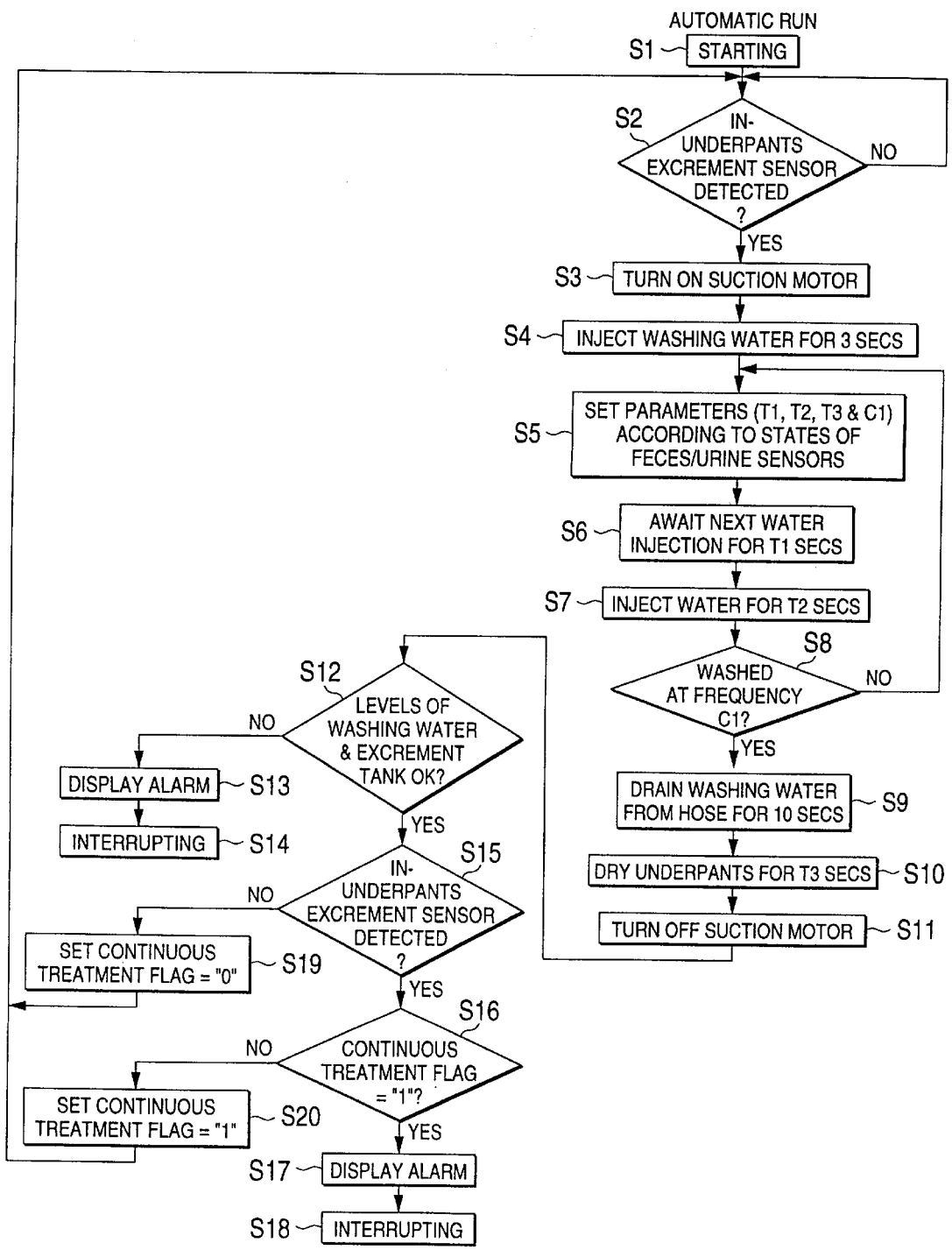
FIG. 2 is a first flow chart for explaining the contents of a program stored in a sequencer shown in FIG. 1.
Figure 3:
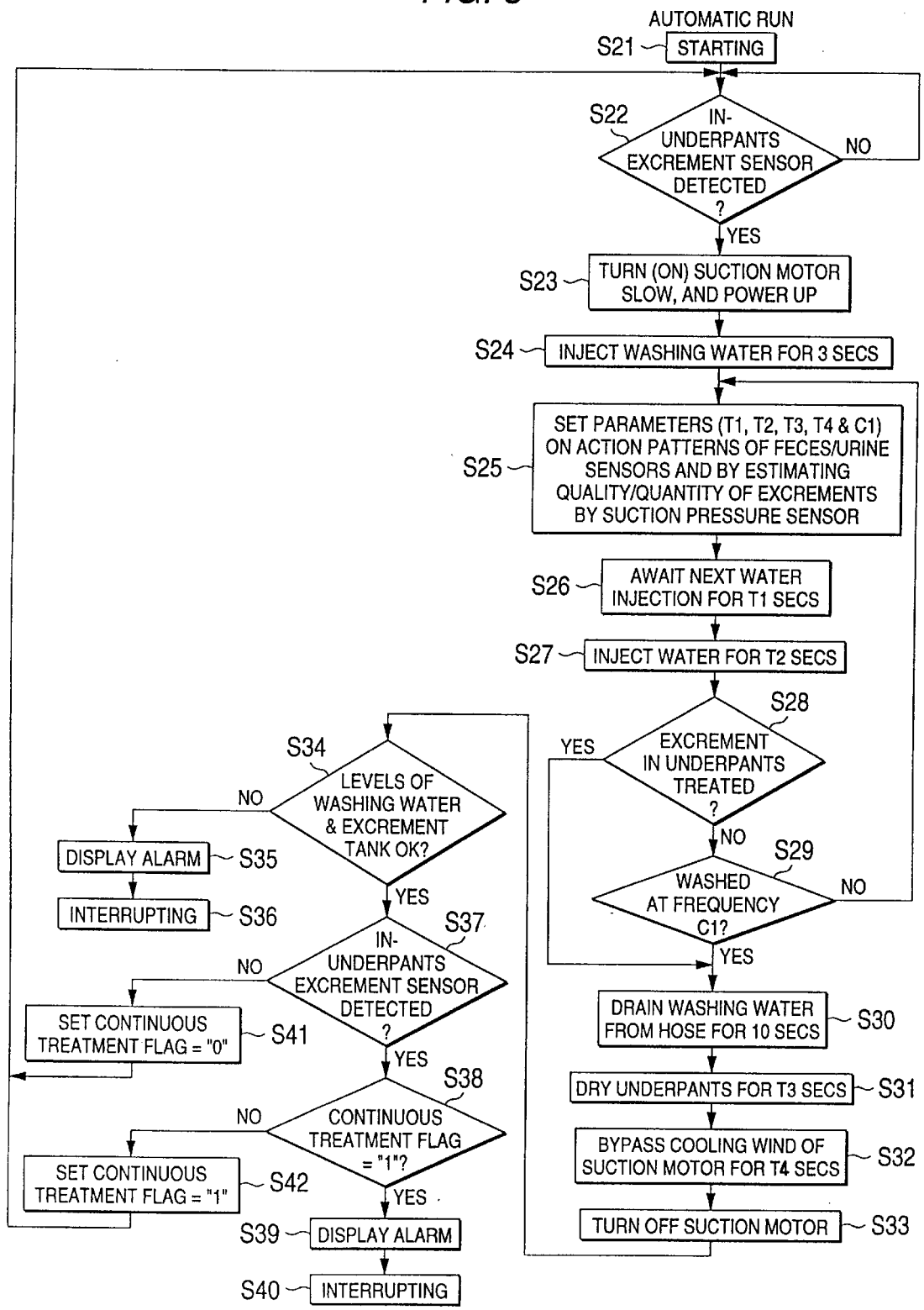
FIG. 3 is a second flow chart which is partially modified from the flow chart shown in FIG. 2.

FIG. 4 is a time chart showing the actions based on the flow chart shown in FIG. 2. The characteristics illustrated in FIG. 4(*a*) indicate the actions of the suction motor 21, and the action time period is controlled by steps S3 and S11 of FIG. 2. On the other hand, the characteristics illustrated in FIG. 4(*b*) indicate the actions of the water supply pump 5. The time parameters T1, T2, T3 and C1 for driving the water supply pump 5 intermittently are set by step S5 of FIG. 2. The characteristics illustrated in FIG. 4(*c*) indicate the action characteristics of a step for draining the washing water, as left in the washing water supply hose 105, after the end of the washing step. This washing water draining step is provided for preventing the cold water from being injected into the diaper cup 1 at a next starting time.

FIG. 5 is a time chart showing the actions based on the flow chart shown in FIG. 3. The characteristics illustrated in FIG. 5(*a*) indicate the actions of the suction motor 21, and the action time period is controlled by steps S23 and S33 of FIG. 3. On the other hand, the characteristics illustrated in FIG. 5(*b*) indicate the actions of the water supply pump 5. The time parameters T1, T2, T3 and C1 for driving the water supply pump 5 intermittently are set by step S25 of FIG. 3. Moreover, the characteristics illustrated in FIG. 5(*c*) indicate the action characteristics of a step for draining the washing water, as left in the washing water supply hose 105, after the end of the washing step, as described above with reference to FIG. 4(*c*). FIG. 5(*d*) illustrates the characteristics for blowing the cooling wind, which has been warmed by the heat generated by the suction motor 21 for a predetermined time period before the suction motor 21 is stopped, to the diaper cup 1, and a time parameter T4, which is set by step S25 of FIG. 3.

As described above, the device for disposing excrement according to the present invention comprises: a diaper cup for enveloping a lumbar/gluteal region of a human body; and a device body connected to the diaper cup for supplying washing water to the inside of the diaper cup and for sucking the excrements and sewage from the inside of the diaper cup. The device for disposing excrement is characterized in that the device body includes: a suction motor for establishing a vacuum to suck the excrements and the sewage; a water supply pump for supplying the washing water; and a sequencer for controlling the suction motor and the water supply pump; and in that the sequencer includes intermittent drive means for controlling the drive of the water supply pump intermittently. As a result, the excrements in a diaper cup can be efficiently washed in a mode matching the kind of the excrements in the diaper cup by discriminating the excrement kind with the feces sensor and the urine sensor.

Moreover, the device is characterized in that the sequencer includes continuous drive means for controlling the drive of the suction motor continuously when the drive of the water supply pump is intermittently controlled by the intermittent drive means. The device is also characterized in that the sequencer includes continuous drive means for controlling the drive to start and transfer to a continuous one by raising the rotating speed of the suction motor gradually. As a result, it is possible to feed the excrements in the diaper cup without delay to the excrement tank and also to lighten the stimulation on the nursed person wearing the diaper cup at the action starting time of the system.

Moreover, the device is characterized in that the diaper cup includes a feces sensor and a urine sensor; and in that the sequencer includes intermittent drive means for controlling the drive of the water supply pump intermittently in a mode according to the sense signals of the feces sensor and the urine sensor. The device is also characterized in that the sequencer includes intermittent drive means for controlling the drive of the water supply pump intermittently by changing the intermittent drive mode of the water supply pump between the case in which the feces sensor senses feces, and the case in which the urine sensor senses urine. The device is further characterized in that the sequencer includes intermittent drive means for changing the time period per water supply of the water supply pump by setting time parameters according to the sense signals of the feces sensor and the urine sensor. As a result, it is possible to wash the excrements without making the wearer of the diaper cup feel uncomfortable, and to promote the excretion of a patient who could not otherwise excrete by stimulating the patient properly with intermittent injections of washing water.

Moreover, the device is characterized in that the sequencer includes initial drive means for starting the intermittent drive of the water supply pump immediately after the drive start of the suction motor. As a result, the inside of the diaper cup and the inside of the excrement suction hose can be wetted with the washing water immediately after a start so that the excrements can be smoothly fed to the excrement tank.

It will be appreciated that the present invention is not limited to the exact construction that has been described above and illustrated in the accompanying drawings, and that various modifications and changes can be made without departing from the scope and spirit thereof. It is intended that the scope of the invention only be limited by the appended claims.

What is claimed is:

1. A device for disposing excrement, comprising:
 a diaper cup for enveloping a lumbar/gluteal region of a human body; and
 a system body connected to said diaper cup for supplying washing water to an inside of the diaper cup and for sucking excrements and sewage from the inside of said diaper cup;
 wherein said system body includes:
  a suction motor for establishing a vacuum to suck the excrements and the sewage;
  a water supply pump for supplying the washing water; and
  a sequencer for controlling said suction motor and said water supply pump, said sequencer having intermittent drive means for controlling a drive of said water supply pump intermittently.

2. The device for disposing excrement as set forth in claim 1, wherein said sequencer includes continuous drive means for controlling a drive of said suction motor continuously when the drive of said water supply pump is intermittently controlled by said intermittent drive means.

3. The device for disposing excrement as set forth in claim 2, wherein said continuous drive means controls the drive of said suction motor to start and transfer to a continuous drive by raising a rotating speed of said suction motor gradually.

4. The device for disposing excrement as set forth in claim 3, wherein said diaper cup includes a feces sensor and a urine sensor, and said intermittent drive means controls the drive of said water supply pump intermittently in a mode according to sense signals of said feces sensor and said urine sensor.

5. The device for disposing excrement as set forth in claim 4, wherein said intermittent drive means controls the drive of said water supply pump intermittently by changing an intermittent drive mode of said water supply pump based on whether said feces sensor senses feces, and whether said urine sensor senses urine.

6. The device for disposing excrement as set forth in claim 5, wherein said intermittent drive means changes a time period per water supply of said water supply pump by setting time parameters according to the sense signals of said feces sensor and said urine sensor.

7. The device for disposing excrement as set forth in claim 6, wherein said sequencer includes initial drive means for starting the intermittent drive of said water supply pump immediately after a drive start of said suction motor.

8. The device for disposing excrement as set forth in claim 1, wherein said sequencer includes continuous drive means for controlling a drive of said suction motor to start and transfer to a continuous drive by raising a rotating speed of said suction motor gradually.

9. The device for disposing excrement as set forth in claim 1, wherein said diaper cup includes a feces sensor and a urine sensor, and said intermittent drive means controls the drive of said water supply pump intermittently in a mode according to sense signals of said feces sensor and said urine sensor.

10. The device for disposing excrement as set forth in claim 9, wherein said intermittent drive means controls the drive of said water supply pump intermittently by changing the intermittent drive mode of said water supply pump based on whether said feces sensor senses feces, and whether said urine sensor senses urine.

11. The device for disposing excrement as set forth in claim 9, wherein said intermittent drive means changes a time period per water supply of said water supply pump by setting time parameters according to the sense signals of said feces sensor and said urine sensor.

12. The device for disposing excrement as set forth in claim 1, wherein said sequencer includes initial drive means for starting the intermittent drive of said water supply pump immediately after a drive start of said suction motor.

13. A device for disposing excrement, comprising:

a diaper cup for enveloping a lumbar/gluteal region of a human body;

a water supply pump connected to said diaper cup for supplying washing water to an inside of the diaper cup;

a suction motor connected to said diaper cup for sucking excrements and sewage from the inside of said diaper cup; and a sequencer for controlling said suction motor and said water supply pump, said sequencer having an intermittent drive means for driving said water supply pump intermittently, and a continuous drive means for driving said suction motor continuously when said water supply pump is being driven intermittently.

14. The device for disposing excrement as set forth in claim 13, wherein said continuous drive means controls the drive of said suction motor to start and transfer to a continuous drive by raising a rotating speed of said suction motor gradually.

15. The device for disposing excrement as set forth in claim 14, wherein said diaper cup includes a feces sensor and a urine sensor, and said intermittent drive means drives the water supply pump intermittently in a predetermined mode based on whether said feces sensor senses feces, and whether said urine sensor senses urine.

* * * * *